United States Patent
Haller et al.

(10) Patent No.: US 8,175,717 B2
(45) Date of Patent: May 8, 2012

(54) ULTRACAPACITOR POWERED IMPLANTABLE PULSE GENERATOR WITH DEDICATED POWER SUPPLY

(75) Inventors: Matthew I. Haller, Valley Village, CA (US); Jordi Parramon, Valencia, CA (US); Emanuel Feldman, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 433 days.

(21) Appl. No.: 11/221,095

(22) Filed: Sep. 6, 2005

(65) Prior Publication Data
US 2007/0055308 A1 Mar. 8, 2007

(51) Int. Cl.
*A61N 1/00* (2006.01)
(52) U.S. Cl. .................................................. 607/61
(58) Field of Classification Search ............... 607/4, 5, 607/30, 33, 61; 365/229
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,731,681 A | 5/1973 | Blackshear et al. | |
| 3,822,708 A | 7/1974 | Zilber | |
| 4,082,097 A | 4/1978 | Mann et al. | |
| 4,408,607 A | 10/1983 | Maurer | |
| 4,408,608 A | 10/1983 | Daly et al. | |
| 4,424,812 A | 1/1984 | Lesnick | |
| 4,548,209 A * | 10/1985 | Wielders et al. | 607/4 |
| 4,556,061 A | 12/1985 | Barreras et al. | |
| 4,590,946 A | 5/1986 | Loeb | |
| 4,608,985 A | 9/1986 | Chrish et al. | |
| 4,612,934 A | 9/1986 | Borkan | |
| 4,628,942 A | 12/1986 | Sweeney et al. | |
| 4,649,936 A | 3/1987 | Ungar et al. | |
| 4,690,144 A | 9/1987 | Rise et al. | |
| 4,690,145 A | 9/1987 | King-Smith et al. | |
| 4,702,254 A | 10/1987 | Zabara | |
| 4,781,893 A | 11/1988 | Dickakian | |
| 4,793,353 A | 12/1988 | Borkan | |
| 4,867,164 A | 9/1989 | Zabara | |
| 5,080,096 A * | 1/1992 | Hooper et al. | 607/30 |
| 5,193,539 A | 3/1993 | Schulman et al. | |
| 5,193,540 A | 3/1993 | Schulman et al. | |

(Continued)

FOREIGN PATENT DOCUMENTS

JP 06-125994 5/1994

(Continued)

OTHER PUBLICATIONS

U.S. Appl. No. 11/003,155, filed Dec. 3, 2004, Fridman.

(Continued)

*Primary Examiner* — George Manuel
(74) *Attorney, Agent, or Firm* — Wong Cabello Lutsch, Rutherford & Brucculeri, LLP

(57) ABSTRACT

A stimulator includes an implantable pulse generator comprising circuit elements, a first power source, such as an ultracapacitor, that provides operating power for the circuit elements of the pulse generator. The pulse generator can also have a memory associated therewith, such as a volatile memory for storing programming data. A second power source that has higher voltage retention than the first power source can also be included. The second power source can be dedicated to the volatile memory and can provide operating power for the volatile memory.

33 Claims, 6 Drawing Sheets

U.S. PATENT DOCUMENTS

| | | | |
|---|---|---|---|
| 5,199,430 A | 4/1993 | Fang et al. | |
| 5,211,129 A | 5/1993 | Taylor et al. | |
| 5,222,494 A | 6/1993 | Baker, Jr. | |
| 5,235,979 A * | 8/1993 | Adams | 607/5 |
| 5,312,439 A | 5/1994 | Loeb | |
| 5,314,458 A | 5/1994 | Najafi et al. | |
| 5,324,316 A | 6/1994 | Schulman et al. | |
| 5,358,514 A | 10/1994 | Schulman et al. | |
| 5,405,367 A | 4/1995 | Schulman et al. | |
| 5,513,636 A | 5/1996 | Palti | |
| 5,515,848 A | 5/1996 | Corbett, III et al. | |
| 5,571,148 A | 11/1996 | Loeb et al. | |
| 5,591,212 A | 1/1997 | Keimel | 607/5 |
| 5,591,217 A | 1/1997 | Barreras | |
| 5,649,970 A | 7/1997 | Loeb et al. | |
| 5,650,974 A * | 7/1997 | Yoshimura | 365/229 |
| 5,700,282 A | 12/1997 | Zabara | |
| 5,713,939 A * | 2/1998 | Nedungadi et al. | 607/33 |
| 5,769,877 A | 6/1998 | Barreras, Sr. | 607/61 |
| 5,938,584 A | 8/1999 | Ardito et al. | |
| 6,051,017 A | 4/2000 | Loeb et al. | |
| 6,154,678 A | 11/2000 | Lauro | |
| 6,164,284 A | 12/2000 | Schulman et al. | |
| 6,198,970 B1 | 3/2001 | Freed et al. | |
| 6,208,894 B1 | 3/2001 | Schulman et al. | |
| 6,216,045 B1 | 4/2001 | Black et al. | |
| 6,219,580 B1 | 4/2001 | Faltys et al. | |
| 6,226,552 B1 | 5/2001 | Staunton et al. | |
| 6,272,382 B1 | 8/2001 | Faltys et al. | |
| 6,308,101 B1 | 10/2001 | Faltys et al. | |
| 6,341,236 B1 | 1/2002 | Osorio et al. | |
| 6,381,496 B1 | 4/2002 | Meadows et al. | |
| 6,505,078 B1 | 1/2003 | King et al. | |
| 6,516,227 B1 | 2/2003 | Meadows et al. | |
| 6,553,263 B1 | 4/2003 | Meadows et al. | |
| 6,631,296 B1 | 10/2003 | Parramon et al. | |
| 6,733,485 B1 | 5/2004 | Whitehurst et al. | |
| 6,856,838 B2 | 2/2005 | Parramon et al. | |
| 6,920,359 B2 | 7/2005 | Meadows et al. | |
| 7,054,689 B1 | 5/2006 | Whitehurst | 607/40 |
| 7,200,504 B1 | 4/2007 | Fister | 702/75 |
| 2002/0055779 A1 | 5/2002 | Andrews | |
| 2002/0099256 A1 | 7/2002 | Manne | |
| 2002/0099419 A1 | 7/2002 | Cohen et al. | |
| 2002/0156462 A1 | 10/2002 | Stultz | |
| 2002/0161415 A1 | 10/2002 | Cohen et al. | |
| 2003/0045914 A1 | 3/2003 | Cohen et al. | |
| 2003/0083698 A1 | 5/2003 | Whitehurst | 607/72 |
| 2003/0236557 A1 | 12/2003 | Whitehurst | 607/48 |
| 2003/0236558 A1 | 12/2003 | Whitehurst | 607/45 |
| 2004/0000416 A1 | 1/2004 | Hou | |
| 2004/0015204 A1 | 1/2004 | Whitehurst | 607/48 |
| 2004/0015205 A1 | 1/2004 | Whitehurst et al. | |
| 2004/0059392 A1 | 3/2004 | Parramon et al. | |
| 2004/0062298 A1 | 4/2004 | McDonough et al. | |
| 2004/0082908 A1 | 4/2004 | Whitehurst et al. | |
| 2004/0088032 A1 | 5/2004 | Haller et al. | |
| 2005/0021108 A1 | 1/2005 | Klosterman et al. | |
| 2005/0057905 A1 | 3/2005 | He et al. | |
| 2005/0107841 A1 | 5/2005 | Meadows | 607/43 |
| 2005/0131496 A1 | 6/2005 | Parramon et al. | |
| 2005/0137651 A1 | 6/2005 | Litvak | 607/57 |
| 2005/0184975 A1 | 8/2005 | Sawada | |
| 2006/0100672 A1 | 5/2006 | Litvak | 607/57 |
| 2006/0106446 A1 | 5/2006 | Fridman | 607/57 |
| 2006/0229688 A1 | 10/2006 | McClure | 607/9 |

FOREIGN PATENT DOCUMENTS

| | | |
|---|---|---|
| JP | 10-509901 | 9/1998 |
| JP | 2000122811 | 4/2000 |
| JP | 2001-322515 | 11/2001 |
| JP | 2002201321 | 7/2002 |
| JP | 2005-164672 | 6/2005 |
| WO | 96/20754 | 7/1996 |
| WO | 98/37926 | 9/1998 |
| WO | 98/43700 | 10/1998 |
| WO | 98/43701 | 10/1998 |
| WO | 02/058782 | 8/2002 |

OTHER PUBLICATIONS

U.S. Appl. No. 11/008,869, filed Dec. 9, 2004, Segel.
U.S. Appl. No. 11/016,604, filed Dec. 16, 2004, Narayan.
U.S. Appl. No. 11/089,171, filed Mar. 24, 2005, Hahn.
U.S. Appl. No. 60/665,171, filed Mar. 24, 2005, Harrison.
U.S. Appl. No. 11/122,648, filed May 5, 2005, Griffith.
U.S. Appl. No. 11/139,296, filed May 26, 2005, Carbunaru.
U.S. Appl. No. 11/178,054, filed Jul. 8, 2005, Faltys.
U.S. Appl. No. 11/226,777, filed Sep. 13, 2005, Faltys.

* cited by examiner

ULTRACAPACITOR POWERED IMPLANTABLE PULSE GENERATOR WITH DEDICATED POWER SUPPLY

TECHNICAL FIELD

The following description relates to implantable pulse generators ("IPG"), and more particularly to an ultracapacitor powered IPG with a dedicated power supply for preserving data integrity.

BACKGROUND

Implantable pulse generators (IPG) are devices that generate electrical stimuli to deliver to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system.

A spinal cord stimulation (SCS) system is a programmable implantable pulse generating system used to treat chronic pain by providing electrical stimulation pulses from an electrode array placed epidurally near a patient's spine. SCS systems consist of several components, including implantable and external components, surgical tools, and software.

Spinal cord stimulation is a well-accepted clinical method for reducing pain in certain populations of patients. SCS systems typically include an implantable pulse generator (IPG) or RF transmitter/receiver, insulated lead wires, and electrodes connected to the leads. The system delivers electrical pulses to the target nerves (e.g., dorsal column fibers within the spinal cord) through the electrodes implanted along the dura of the spinal cord. The leads exit the spinal cord and are tunneled around the torso of the patient to a subcutaneous pocket where the pulse generator/RF receiver is implanted.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neural stimulation of the spinal cord. A relatively thin and flexible strip of physiologically inert plastic is provided with a plurality of electrodes formed thereon. The electrodes are connected by leads to a RF receiver, which is also implanted and controlled by an external controller. The implanted RF receiver has no power storage means, and must be coupled to the external RF transmitter/controller in order for neural stimulation to occur.

In U.S. Pat. No. 3,822,708, another type of electrical spinal cord stimulating device is shown. The device has five aligned electrodes that are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of from 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

The concern over how to power an IPG has also been addressed in various ways. For example, in U.S. Pat. No. 4,408,607, a type of capacitive energy source for an implanted medical device is disclosed. The power supply has a rechargeable capacitor that is used as the principal power source. The power source includes a lithium battery that is used as a second, or alternative, power source. The lithium battery replaces the capacitor as a power source during the charging period for the capacitor. This allows for continuous use of the device.

Regardless of past innovations, unique problems continue to be associated with providing power to IPGs, mainly because it is necessary to provide power to the device implanted below the skin. Commercial SCS systems are powered by one of three sources; a primary battery, a rechargeable battery, or an oscillating magnetic field (RF power). Since the device is subcutaneously implanted in a patient, either a bulky, external power source is used or an implanted power source must support device operation for a reasonable period of time in order to reduce further surgical trauma to the patient. RF powered devices suffer from poor patient acceptance due to the requirement of wearing an external device at all times.

If a battery is used as the energy source, it must have a large enough storage capacity to operate the device for a reasonable length of time. For low-power devices (less than 100 .u.W) such as cardiac pacemakers, a primary battery may operate for a reasonable length of time, often up to ten years. However, in many neural stimulation applications such as SCS, the power requirements are considerably greater due to higher stimulation rates, pulse widths, or stimulation thresholds. Powering these devices with conventional primary batteries would require considerably larger capacity batteries to operate them for a reasonable length of time (5 or more years), resulting in devices so large that they may be difficult to implant or, at the very least, reduce patient comfort. Therefore, in order to maintain a device size that is conducive to implantation, improved primary batteries with significantly higher energy densities are needed. However, given the state of the art in battery technology, the required energy density is not achievable at the present time.

For many neurostimulation applications, typical primary cells, such as non-rechargeable lithium thionyl chloride batteries are used, but they suffer from poor device lifetime causing the need for replacement surgeries. This means that during a twenty-five year period of time, a patient may be exposed to us to ten explant surgical procedures for the purpose of battery replacement. Not only is this inconvenient and costly, but as a surgical procedure, it necessarily involves some risk of infection or other complications.

One alternative power source is the secondary, or rechargeable battery, where the energy in these batteries can be replenished by transcutaneously recharging the batteries on a periodic basis. It is known in the art to use a rechargeable battery within an implant device. See, e.g., U.S. Pat. No. 4,082,097, entitled "Multimode Recharging System for Living Tissue Stimulators", and U.S. Pat. No. 6,208,894, entitled "System of Implantable Devices for Monitoring and/or Affecting Body Parameters", which patents are incorporated herein by reference. The devices and methods taught in this patent and application, however, comprise specialized devices, e.g., microstimulators, or relate to specific applications, e.g., cardiac pacing, which impose unique requirements not applicable to many IPG applications.

With the recent development of high capacity rechargeable power sources, rechargeable implantable pulse generators are possible. Due to the large energy density and the toxicity of the battery electrolyte, these batteries are typically contained within a hermetically sealed titanium case.

Super capacitors have been proposed as a replacement option for typical primary cell battery and RF power. One advantage of super capacitors is that they can be recharged approximately 500 times more than a rechargeable battery. This is a significant extension of lifespan over a rechargeable battery, and would substantially reduce the number of surgical procedures required for replacing batteries. Another advantage of super capacitors is their ability to be recharged very quickly.

Super capacitor technology, however, has not advanced enough to reduce super capacitors to a size that could be useful in an implanted IPG. The size of a super capacitor that is able to hold a charge for a reasonable amount of time—even for a twenty-four hour period—is too large to be integrated into an IPG that can be implanted, for example, in an individual's head.

In addition to the problem of applying an appropriate power source to run an IPG for a reasonable length of time, another problem exists with respect to powering IPGs. This problem relates to the loss of volatile memory, such as programming data, whenever the device is discharged. For example, U.S. Pat. No. 5,591,217 describes an implantable stimulator powered by large capacitors that can power the device for eight hours up to a few days. However, when the power source is drained, all programming data is lost and would need to be reloaded at each recharge cycle.

SUMMARY

The present inventors recognized a need for implantable neurostimulation devices, systems and methods that use power sources with significantly longer life spans and solve other known issues.

In one aspect, a stimulator includes an implantable pulse generator comprising circuit elements, a first power source, such as an ultracapacitor, that provides operating power for the circuit elements of the pulse generator. The pulse generator can also have a memory associated therewith, such as a volatile memory for storing programming data. A second power source that has higher voltage retention than the first power source can also be included. The second power source can be dedicated to the volatile memory and can provide operating power for the volatile memory.

In another aspect, a system for stimulating tissue includes an implantable stimulator, a remote programmer unit, and a remote recharge transmitter. The implantable stimulator includes a pulse generator, electronic circuitry that performs a desired circuit function, a first power source, a volatile memory for storing programming data, and a second power source that has higher voltage retention than the first power source. The first power source can provide operating power for the electronic circuitry, and the second power source can be dedicated to the volatile memory and can provide operating power for the volatile memory. The remote programmer unit transmits programming information to the implantable stimulator, and the programming information is stored in the volatile memory. The remote recharge transmitter transmits one or more sets of RF signals to the stimulator to recharge the ultracapacitor and/or the second power source.

DESCRIPTION OF DRAWINGS

Like reference symbols in the various drawings indicate like elements.

DETAILED DESCRIPTION

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from deriving its operating power from an ultracapacitor.

Further, while the invention is described in connection with its use within an SCS system, it is noted that a complete description of the SCS system is not provided herein. Rather, only those portions of the SCS system that relate directly to the present invention are disclosed. A more complete description of an SCS system may be found in U.S. Pat. No. 6,516,227, which is incorporated herein by reference in its entirety.

Figure 1:
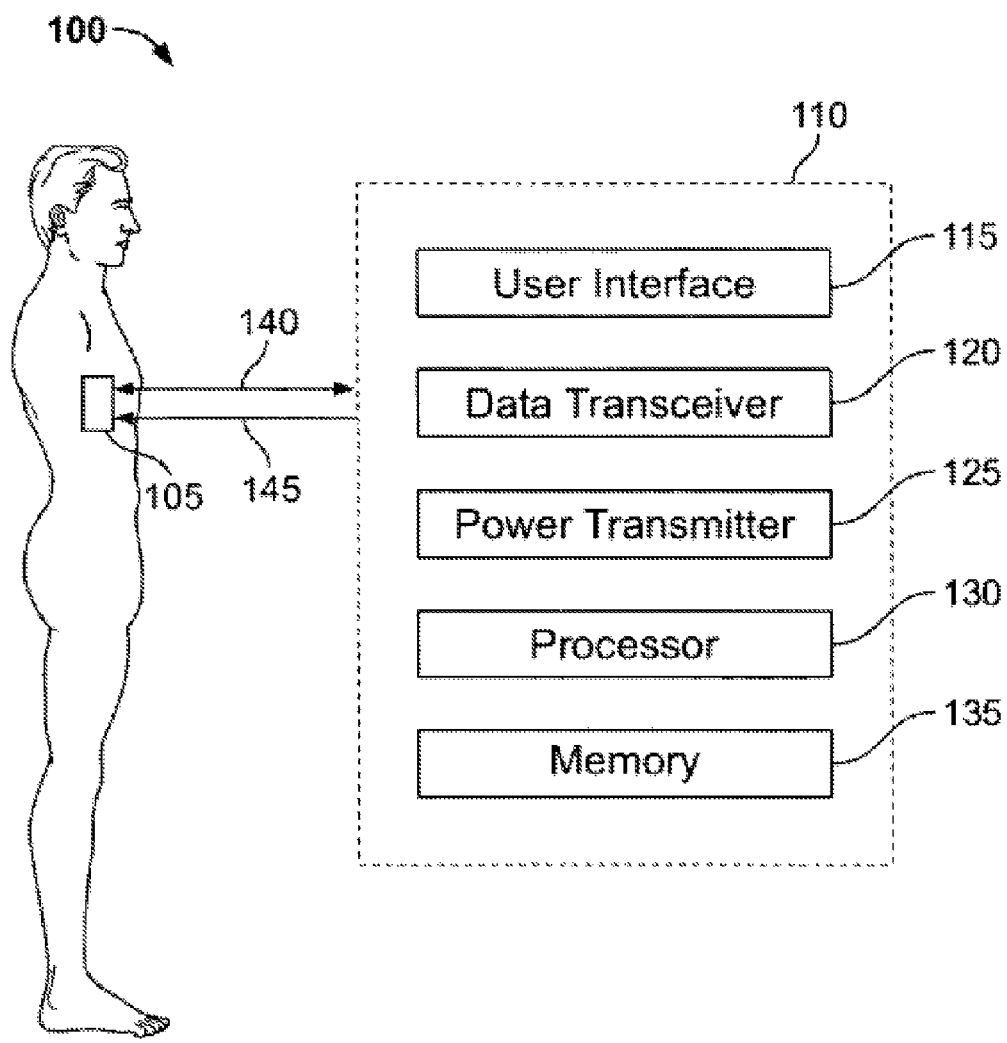
FIG. 1 illustrates a system for stimulating tissue.

FIG. 1 generally shows a system 100 for stimulating tissue. System 100 can stimulate tissue directly to elicit a desired response. The desired response can be inhibitory or excitatory. System 100 can deliver one or more of, e.g., electrical stimuli, chemical stimuli, thermal stimuli, electromagnetic stimuli, and/or mechanical stimuli to elicit the desired response in any of a number of different settings. In one implementation, system 100 can be a spinal cord stimulation system, such as that depicted in FIG. 3.

System 100 can include an implanted portion 105 and an external (i.e., extracorporeal) portion 110. Implanted portion 105 is a device that is adapted for implantation in a body. For example, implanted portion 105 can include a biocompatible housing adapted to reduce the immune response and/or cell necrosis associated with the implantation of portion 105. Implanted portion 105 can stimulate tissue using one or more stimuli for therapeutic, diagnostic, and/or functional purposes. For example, implanted portion 105 can stimulate tissue by electrically exciting the depolarization of a nerve and/or muscle tissue. As another example, implanted portion 105 can stimulate tissue by delivering inhibitory chemical stimuli. As yet another example, implanted portion 105 can deliver light or other electromagnetic stimuli to stimulate photosensitive tissue. As discussed further below, implanted portion 105 can include one or more delivery elements to deliver stimuli to tissue. The delivery elements can include, e.g., electrodes, drug delivery elements, heaters, coolers, light sources, fiber optics, and/or mechanical elements such as piezoelectric elements, balloons, MEMS devices, and the like.

In some implementations, implanted portion 105 can be implanted in a body using one or more surgical insertion tools tailored for the implantation of portion 105. Alternatively, implanted portion 105 can be implanted using commercially available surgical equipment, such as hypodermic needles, conventional surgical equipment, and endoscopic or laparoscopic devices.

In some implementations, implanted portion 105 can operate independently (i.e., as a solitary implanted device) or implanted portion 105 can operate as part of an implanted system of devices whose activities are coordinated to achieve therapeutic, diagnostic, and/or functional purposes.

In some implementations, implanted portion 105 can receive data from one or more sensing devices (not shown) that respond to one or more conditions of the body in which implanted portion 105 is implanted. Example sensing devices include chemical sensors, electrodes, optical sensors, mechanical (e.g., motion, pressure) sensors, and temperature sensors. The received data can be used, alone or in conjunction with data received from external devices and/or other implanted devices, by implanted portion 105 in controlling the stimulation of tissue.

External (extracorporeal) portion 110 is a device for providing user interaction with implanted portion 105. External portion 110 is generally situated outside the body in which implanted portion 105 is implanted. External portion 110 can include a user interface 115, a data transceiver 120, a power transmitter 125, a processor 130, and a memory 135. User interface 115, data transceiver 120, power transmitter 125, processor 130, and memory 135 can be housed in a single housing or in multiple housings. User interface 115, data transceiver 120, power transmitter 125, processor 130, and memory 135 can be linked for data communication and control by one or more wired (e.g., wires, busses, optical fiber) or wireless (e.g., infrared, WiFi, radio frequency (RF)) data links.

User interface 115 can include one or more input/output devices for interacting with a user. For example, input/output devices can be mechanical, audio, and/or visual devices, including keypads, touch- and display-screens, speakers, and data ports.

Data transceiver 120 communicates with implanted portion 105 over a data link 140. This communication can include both the transmission and reception of data, including data that represents commands received from a user over user interface 115 and data regarding the operational status and history of implanted portion 105. For example, data that represents the boundaries on stimulation parameters, the current operational settings of stimulation parameters, and whether or not implanted portion 105 is currently stimulating tissue can be communicated over data link 140.

Data transceiver 120 may thus include both a transmitter and a receiver. Data transceiver 120 can be a wireless transceiver in that transceiver 120 communicates with implanted portion 105 without the use of a transdermal physical link. For example, data transceiver 120 can communicate with implanted portion 105 using sound and/or electromagnetic radiation (e.g., light or radio waves) that propagates through a body to and from implanted portion 105.

Power transmitter 125 relays energy to implanted portion 105 over a power link 145. The energy relayed from transmitter 125 can be captured and stored in implanted portion 105 and subsequently converted into one or more stimuli for stimulating tissue. The relayed energy can include electrical energy, magnetic energy, electromagnetic energy, and/or mechanical energy. Power transmitter 125 can be a wireless transmitter in that transmitter 125 relays energy to implanted portion 105 without the use of a transdermal physical link.

Processor 130 is a data processing device that performs processing activities in accordance with logic established by a set of instructions. The instruction can be embodied in hardware and/or software. For example, the processor 130 can be a microprocessor, FPGA's, ASIC's, and/or a set of logic elements arranged to embody the instructions.

The instructions performed by processor 130 can implement operations associated with controlling the stimulation of tissue. These operations can include the management of interactions with a user over user interface 115, the communication of data with implanted portion 105 over data transceiver 120, and the relaying of energy to implanted portion 105 over power transmitter 125. These operations can also include various processes described below.

Memory 135 is a storage device that can store instructions and/or data for controlling the stimulation of tissue in machine-readable format. Memory 135 can be accessed by one or more of user interface 115, data transceiver 120, power transmitter 125, and processor 130 to store and/or retrieve instructions and/or data. Memory 135 can include a memory controller or other interface to facilitate such exchanges of information.

One class of data that can be stored in memory 135 is a stimulation parameter. A stimulation parameter characterizes the stimulation to be delivered by implanted portion 105. A stimulation parameter can characterize the stimulation to be delivered in a number of different ways. For example, a stimulation parameter can be a particular value (e.g., "15"), a reference to another value (e.g., "15 more than a reference value"), and/or a reference to a memory location or other discrete value (e.g., "the third element in the list [5, 10, 15, 20]"). Stimulation parameter can be identified using the values themselves (e.g., "the stimulation parameter is 5.0") or using comparisons (e.g., "the stimulation parameter is less than 5.0").

A stimulation parameter can characterize stimuli delivered by implanted portion 105 directly, or a stimulation parameter can characterize one or more aspects of the operation of implanted portion 105 that impacts the delivered stimuli. Examples of operational aspects that impact the delivered stimuli include the setting or calibration of a timer circuit or the selection of a particular power supply or stimulus delivery element (such as an electrode) when more that one is available.

Figure 2A:
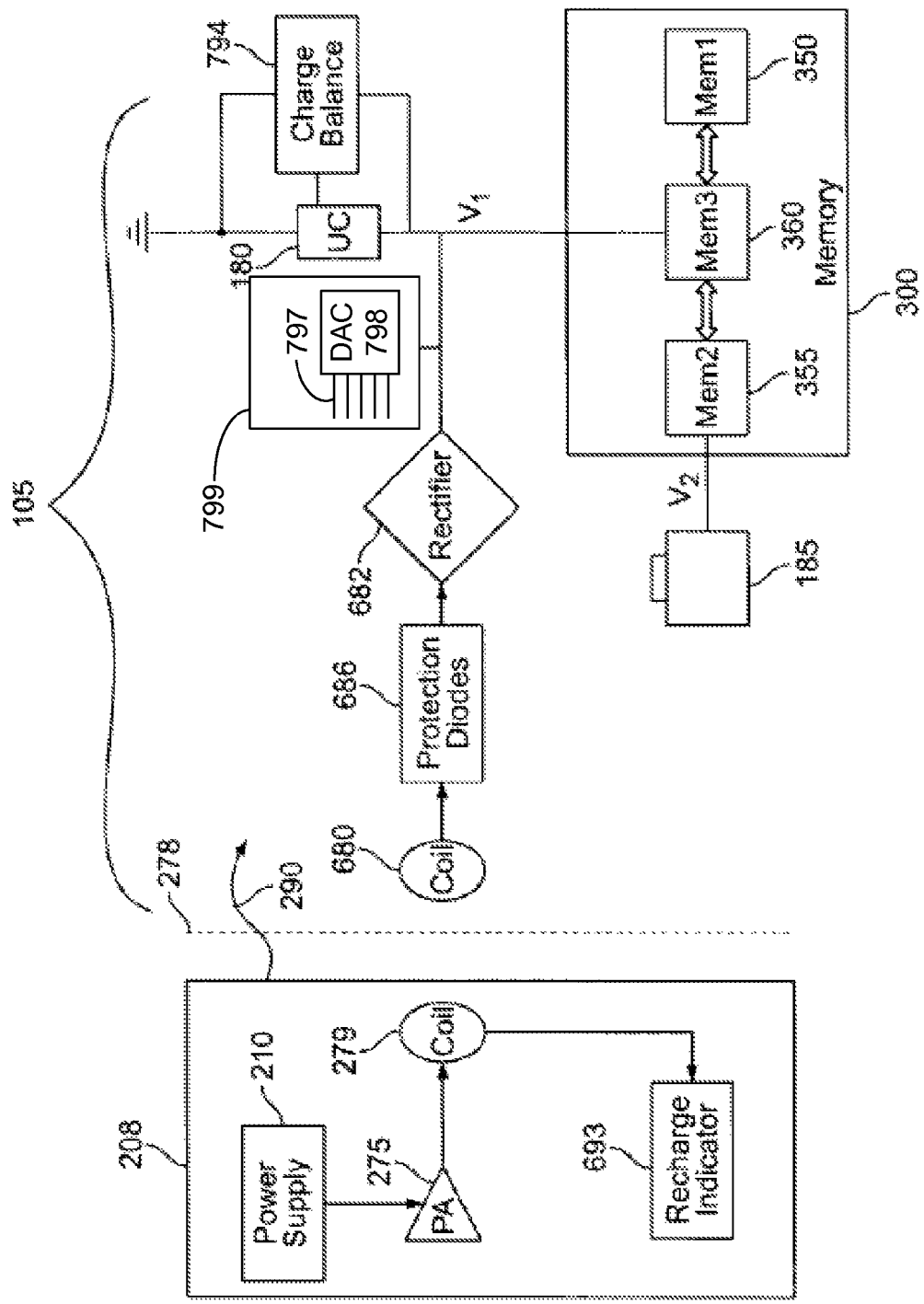
FIG. 2A is a block diagram representing a system for stimulating tissue in accordance with one embodiment.
Figure 2B:
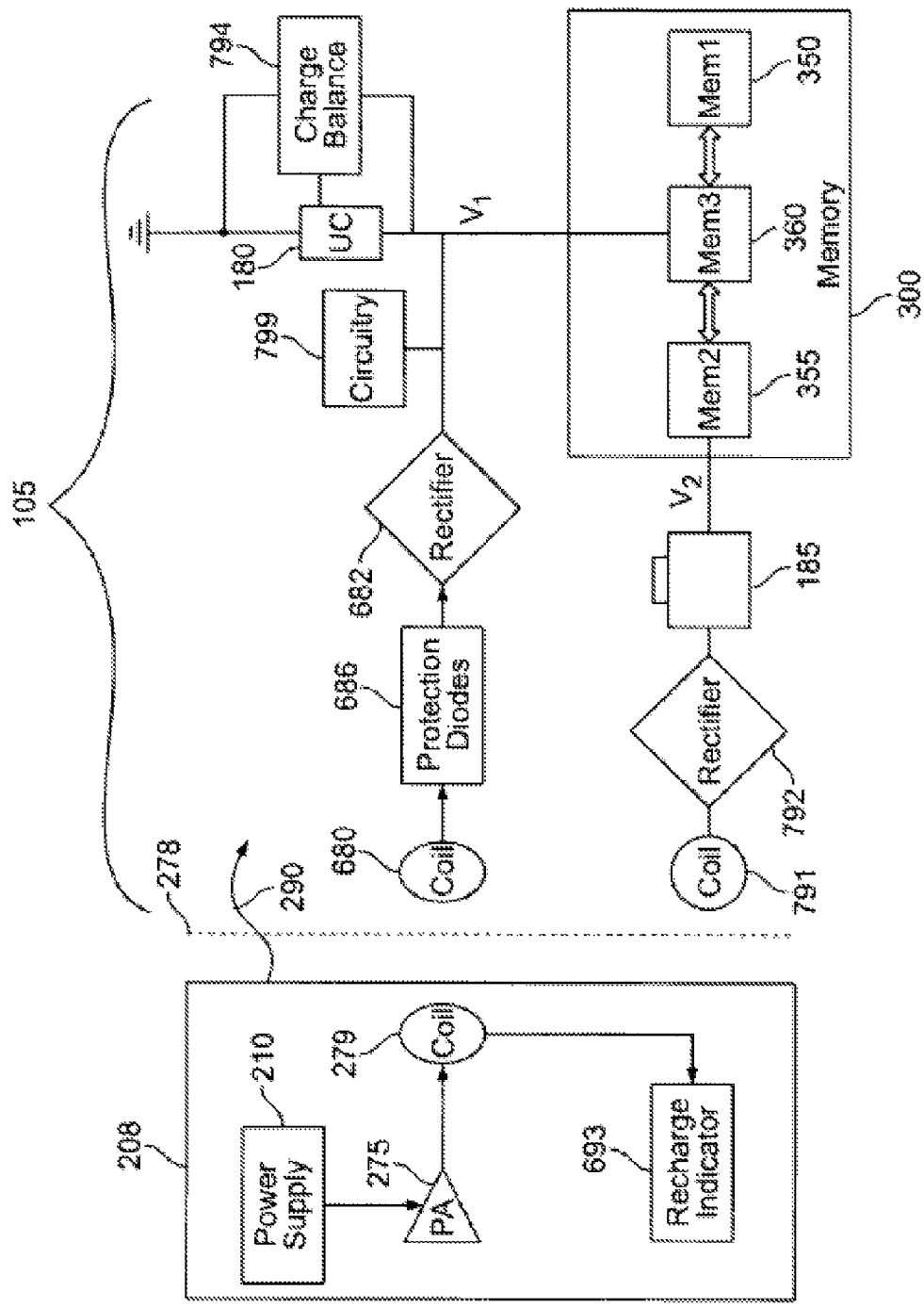
FIG. 2B is a block diagram representing a system for stimulating tissue in accordance with another embodiment.

Turning next to FIGS. 2A and 2B, block diagrams of systems for stimulating tissue are shown. As shown in FIGS. 2A and 2B, the IPG 105 is implanted under the patient's skin 278. The IPG 105 includes a replenishable power source 180, such as an ultracapacitor. It is this ultracapacitor 180 that must be replenished or recharged on a regular basis, or as needed, so that the IPG 105 can carry out its intended function.

To that end, the recharging system of the present invention uses the portable external refresh-recharge transmitter unit 208 to couple energy, represented in FIGS. 2A and 2B by the wavy arrow 290, into the IPG's power source 180. The portable external charger 208, in turn, obtains the energy 290 that it couples into the power source 180 from its own power supply 210. The power supply 210 can be a wall outlet supplying AC power or a power supply that supplies DC power, such as a rechargeable battery or a regular battery. The refresh-recharge transmitter unit 208 can include an ON/OFF switch (not shown), a low battery light or LED (not shown), a "stimulator full" light or LED (not shown), a recharge indicator 693, such as an audible alarm, speaker, vibrator, or LED, an RF inductor power coil 279, and an antenna (not shown).

A power amplifier 275 can be included within portable external refresh-recharge transmitter unit 208. The power amplifier enables the transfer of energy from the power source 210 to the ultracapacitor 180. If the power source supplies DC power, the circuitry 275 can include DC-to-AC conversion circuitry. The circuitry can therefore covert DC power from the battery to an AC signal that may be inductively coupled through external coil 279 in the transmitter unit 208 with another coil 680 included within the IPG 105, as is known in the art. External coil 279 essentially emits RF waves establishing EMF wave fronts which are received by coil 680. Although specific embodiments of a transmitter unit 208 have been described herein, other embodiments known in the art can also be used. For example, U.S. Pat. No. 6,516,227 ("'227 patent"), which is incorporated herein by reference in its entirety, describes external transmitters that can be used to recharge the IPG 105 described herein.

The external transmitter unit 208 can include a recharge indicator 693 that operates in conjunction with a back telemetry receiver (not shown). The back telemetry receiver receives signals from a back telemetry transmitter in the IPG 105 (not shown), which provides information about the charge level of the battery 185 and/or the ultracapacitor 180. Reference is made to the '227 patent for further description of a back telemetry system that can be used to transmit data and recharge information between the IPG 105 and the external transmitter 208. In another embodiment, the recharge indicator works in conjunction with a timer in the external transmitter (not shown). The timer controls the operation of the recharge indicator 693. The timer can be set at a period of time sufficient for full recharge of the battery 185 and/or the ultracapacitor 180. For example, if the ultracapacitor is the only rechargeable power source in the IPG, the timer can be set at approximately ten seconds, which is sufficient time to recharge the ultracapacitor 180. After ten seconds of recharging, the recharge indicator 693 may be activated to inform the user that the ultracapacitor 180 is recharged.

From FIG. 2A, it is seen that the charging system consists of external charger circuitry 208, used on an as-needed basis, and implantable circuitry contained within the IPG 105. In the charger 208, the power source provides a voltage source for the power amplifier 275 to drive the primary coil 279 at a resonant frequency. The secondary coil 680, in the IPG 105, is tuned to the same resonant frequency.

Upon receipt of an AC signal within the IPG 105, the inductor coil 680 provides a voltage source, and protection diodes 686 are used to protect the circuit elements from an overvoltage condition by keeping the voltage under a certain level, e.g., 5V. A rectifier 682 converts the AC signal into a DC signal, which is used to replenish the ultracapacitor 180 of the implant 105. The charge balance circuitry 794 consists of an operational amplifier (Op Amp) and four resistors. The charge balance circuitry 794 maintains equal voltage across the two capacitors, resulting in a balanced ultracapacitor stack, and prevents any capacitor from experiencing an ultracapacitor-overvoltage condition. The layout of the charge balance circuitry 794 is shown in more detail in FIG. 4.

The power from the ultracapacitor 180 is used to power the implant 105 aside from volatile memory 355 (as described below). For instance, ultracapacitor 180 powers stimulation circuitry 799, which drives the stimulation provided by the implant 105. Various types of stimulation circuitry known to those of skill in the art can be used. For example, the '227 patent provides details of stimulation circuitry, which are incorporated herein. As disclosed in the '227 patent, and as shown in FIG. 2A, stimulation circuitry 799 can comprise one or a plurality of digital-to-analog converters (DACs) 798, which produce analog stimulation pulses at the electrodes of particular amplitudes as set by digital signals 797.

The implantable portion 105 further includes memory 300, which can include several types of memory that can be used to provide the IPG 105 with various operating features. For example, memory 300 can include non-volatile memory 350 for storing, e.g., calibration data. Memory 350 can be read-only-memory (ROM) programmed by the manufacturer of the system 100 or an electrically erasable programmable read-only memory (EEPROM). Memory 300 can also include volatile memory 355 that is programmable by a physician or clinician. Memory 355 is only infrequently changed based on a reevaluation of the patient and treatment. Memory 355 can be a volatile memory including a random access memory (RAM) such as static RAM (SRAM), dynamic RAM (DRAM), or the like. Memory 300 can also include operating memory 360 that can communicate efficiently with memory 350 and memory 355 via registers and stacks. Memory 360 can include CMOS logic, thin-film memories or flip flop registers.

Memory 300 is powered by both the ultracapacitor 180 and a secondary power source 185. The ultracapacitor 180 powers memory 350 and 360, while memory 355 is powered by the secondary power source 185. Thus, even in the event that all power from the ultracapacitor 180 is drained before it is recharged, the secondary power source 185 continues to power memory 355. In this way, the volatile memory 355 is not lost, thus avoiding the need to reprogram the data.

Figure 4:
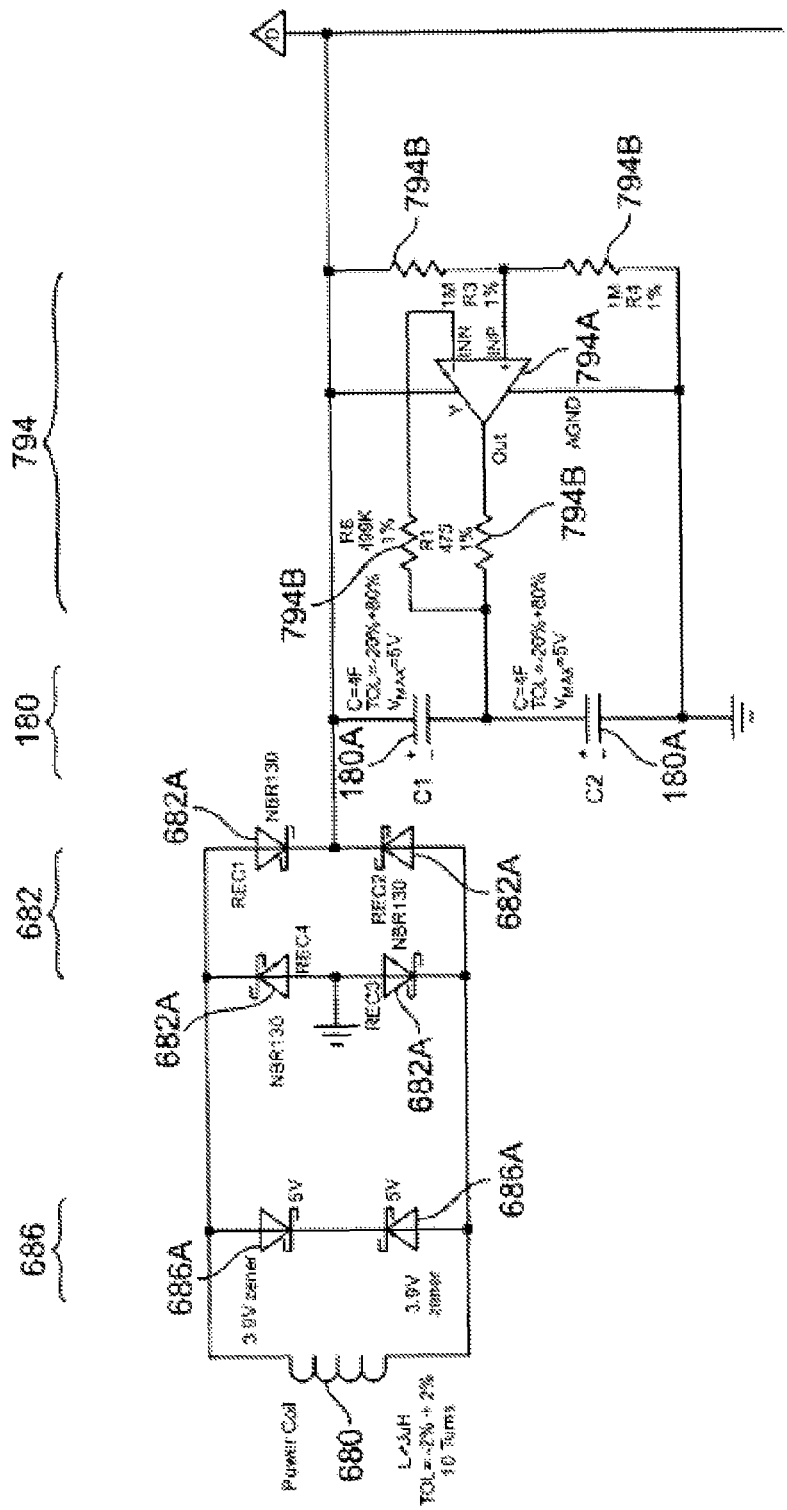
FIG. 4 is a circuit diagram depicting a power circuit associated with an implantable pulse generator in accordance with one embodiment.

Turning now to FIG. 4, a circuit diagram of one embodiment of a recharge circuit of an IPG is shown. The circuit can include a voltage protection component 686, a rectifier component 682, an ultracapacitor component 180, and a charge balance component 794. As shown in FIG. 4, an inductor coil 680 receives an AC signal and provides a voltage source for the IPG. The voltage protection component 686 can include a pair of Zener diodes 686A to keep the voltage under a certain level, e.g., 5V. In other words, the diodes 686A prevent the output voltage from exceeding a threshold value. One of the diodes 686A is forward biased, and the other is reverse biased. One example of diodes that can be used are 5 Watt Zener diodes available from Surmetic as part number 1N5333B. In one embodiment, if the voltage exceeds (3.9V+Vf)→5.1V (i.e., approximately 5V), then it is clipped at 5.1V or approximately 5V. The rectifier component 682 can include a full-wave rectifier bridge to convert the AC signal into a DC signal in order to charge the ultracapacitor 180. The rectifier bridge can include four diodes 682A. An example of rectifiers than can be used are surface mounted Schottky power rectifiers, sold as part number MBR130T1 or MBR130T3.

The ultracapacitor component 180 includes an ultracapacitive power source. The ultracapacitive power source can be a high value, small size capacitive energy device comprising a single capacitor or a plurality—two or more—of serially connected capacitors 180A (as shown in FIG. 4) having a capacitive rating of greater than 0.1 farad, greater than 1 farad, greater than 5 farads, greater than 8 farads or great than 10 farads and limited in volumetric size to less than 50 cubic centimeters, less than 30 cubic centimeters, less than 10 cubic centimeters, less than 5 cubic centimeter, less than 1 cubic centimeter or less than 0.1 cubic centimeter. In one embodiment, the ultracapacitor 180 can be a 2.5V, 10 Farad ultracapacitor available from Maxwell Technologies under the trademark Boostcap and part number PC10. The Boostcap PC10 has about a ten year life capability with over 500,000 duty cycles. It is hermetically sealed and has a low profile prismatic shape.

The charge balance component 794 can include an operational amplifier 794A coupled to four resistors 794B. The four resistors 794B maintain equal voltage across the two capacitors 180A that form the ultracapacitor 180.

The secondary power source 185 can be a battery than has higher voltage retention than the ultracapacitor 180. For example, the ultracapacitor 180 may retain voltage for one day while the battery 185 may retain voltage for one month. As another example, the ultracapacitor 180 may retain voltage for one month while the battery 185 may retain voltage for 10 years. In one embodiment, the secondary power source 185 can be a lithium battery, such as a Sanyo CR1220 lithium battery, which should have a voltage retention of greater than 10 years. In another embodiment, the secondary power source is a rechargeable battery, such as a rechargeable lithium battery. FIGS. 2A and 2B show secondary power source 185 as a battery. If the secondary power source 185 is a rechargeable battery, then a second inductor coil 791 and second rectifier 792, as shown in FIG. 2B, are used to transmit power to recharge the battery 185. The second inductor coil 791 receives an AC signal from a second coil 280 in the external transmitter 208. Thus, the AC signal received by the inductor coil 791 is separate from the AC signal received by the inductor coil 680. The inductor coil 791 provides a voltage source, and rectifier 792 converts the AC signal into a DC signal, which is used to replenish the battery 185 of the implant 105.

Figure 3:
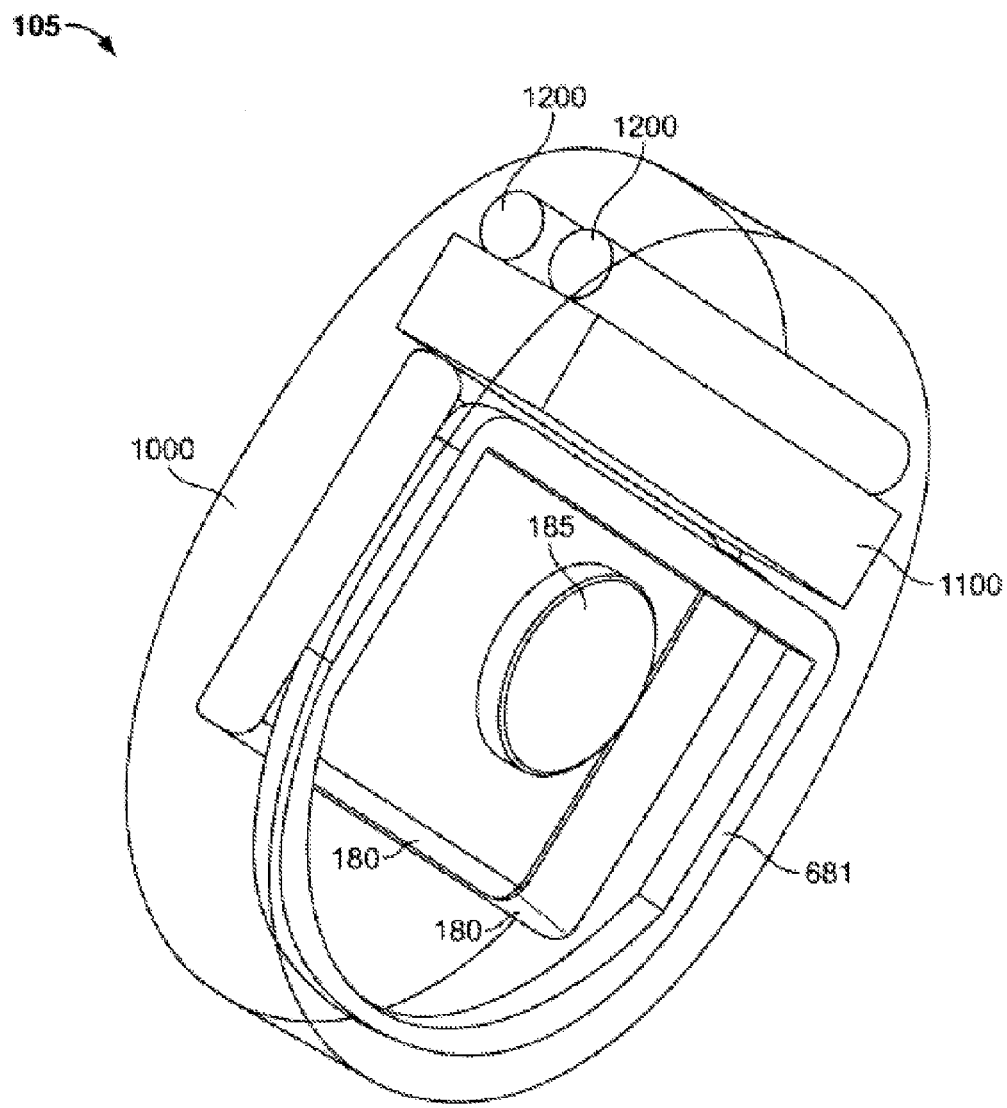
FIG. 3 is a perspective view of an implantable pulse generator in accordance with one embodiment.

As described above with respect to FIG. 2A, the stimulator 105 includes a recharge coil 680. As shown in FIG. 3, the recharge coil 680 may be enclosed in its own case 681 that is made of a magnetically-transparent material (e.g., PEEK®, ceramic, Hysol®, epoxy, silicone, or the like, alone or in combination), or may be enclosed in the stimulator housing which may be made entirely of one or more of those same magnetically-transparent materials, or may be enclosed in the header of implant 105, which may be made of one or more of those same magnetically-transparent materials. Such use of magnetically-transparent material limits heat-generating eddy currents induced in the stimulator 105 during recharging by the external AC magnetic fields. Thus, the recharge rate does not need to be artificially governed to avoid damage caused by excessive heat, reducing recharge time for ultracapacitor 180 to less than a few seconds every twenty-four hours.

FIG. 3 provides an illustration of one example of implant 105. The implant includes a housing 1000, and packaged within the housing is the battery 185, an ultracapacitor 180, and a recharge coil encased in case 681, all of which have been described above. Lead connectors 1200 and hermetically sealed electronics package 1100 are also included.

Figure 5:
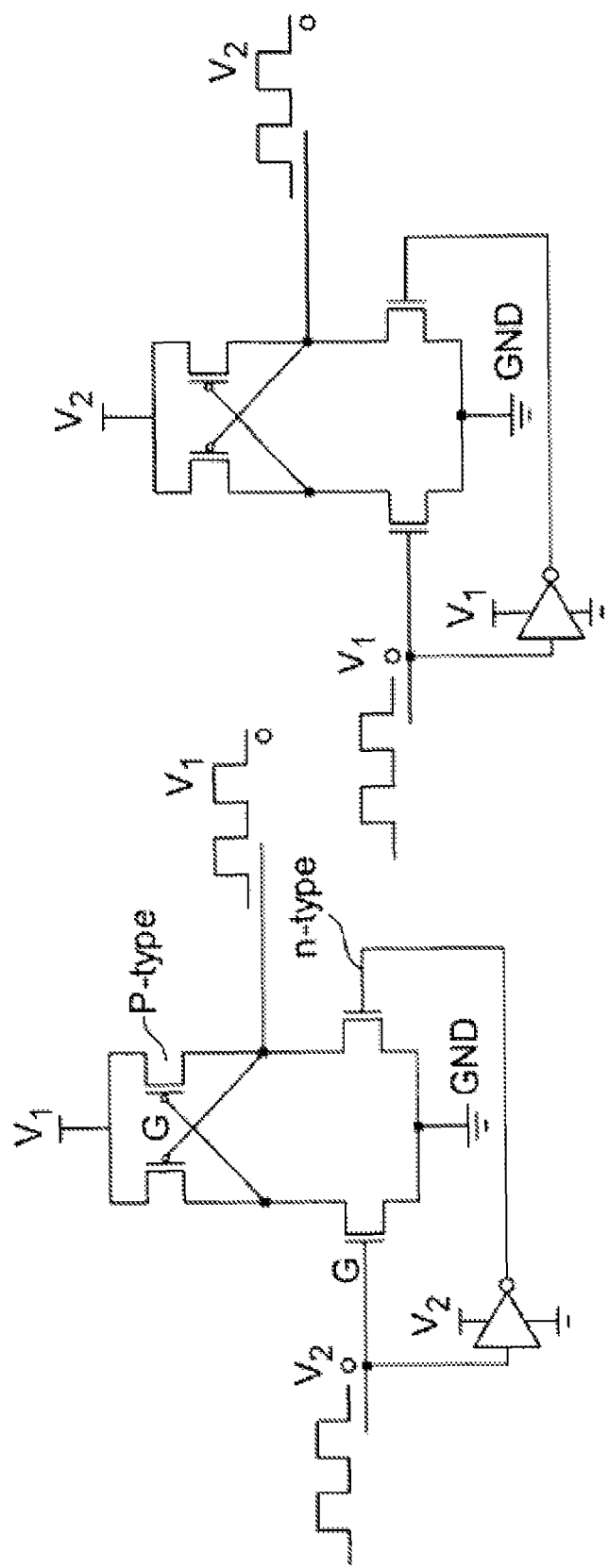
FIG. 5 is a schematic diagram of an isolation circuit in accordance with one embodiment.

FIG. 5 shows the schematics of an exemplary CMOS DC isolation circuit used to provide electrical isolation between the battery 185 and the ultracapacitor 180. A CMOS device contains a p-type metal-oxide-semiconductor (p-MOS) transistor and an n-type MOS (n-MOS) transistor to make up a complementary-MOS (CMOS) circuit. The input to a CMOS circuit is typically to the gate of the input MOS transistor, which exhibits a very high resistance. Therefore, CMOS gates operate essentially with infinite DC impedance and prevent current flow when no voltage is applied to the CMOS gate.

Specifically, the first diagram in FIG. 5 depicts an electrical isolation circuit between V2 and V1 utilizing two CMOS gates and a logic inverter ("NOT" gate). When the voltage at V2 is high, the combination of CMOS gates and the logic inverter ensures that the voltage at V1 remains high as well. On the other hand, when the voltage at V2 is zero, the logic inverter will output a high voltage and pull down the voltage at V1 to ground, resulting in zero voltage for both V1 and V2. The second diagram in FIG. 5 depicts a similar circuit using CMOS gates and a logic inverter to ensure that when V1 is high, V2 will also remain high and when V1 is zero, V2 will also be zero. This circuitry ensures that only the battery 185 powers memory 355. Also, this configuration provides an interface between two circuits at two different voltages (the battery voltage changes very slowly while the supercapacitor voltage fluctuates up and down) and allows the two circuits to communicate while maintaining DC isolation.

Other configurations of stimulator 105 are possible. For example, stimulator 105 can deliver other stimuli such as one or more chemical stimuli, thermal stimuli, electromagnetic stimuli, and/or mechanical stimuli. Stimulator 105 can thus include other stimulus delivery elements.

In other implementations, stimulator 105 can be part of a cochlear implant, a deep brain stimulator, a drug pump, a micro-drug pump, or any other type of implantable stimulator configured to deliver electrical and/or other stimuli. Example spinal cord stimulators include those described in U.S. Pat. Nos. 6,381,496, 6,553,263, and 6,516,227, the contents of all of which are incorporated herein by reference. Example cochlear implants include those described in U.S. Pat. Nos. 6,219,580, 6,272,382, and 6,308,101, the contents of all of which are incorporated herein by reference. Example deep brain stimulators include those described in U.S. Pat. No. 6,920,359, the contents of which are incorporated herein by reference. Example drug pumps include those described in U.S. Pat. Nos. 3,731,681 and 4,781,893, the contents of which are incorporated herein by reference. Example micro-drug pumps include those described in U.S. Patent Application Publication Nos. 2002/0156462 A1 and 2004/0082908 A1, the contents of which are incorporated herein by reference.

Other embodiments are within the scope of the following claims.

What is claimed is:

1. A stimulator comprising:
    an implantable pulse generator comprising circuit elements for producing stimulation pulses, wherein the circuit elements comprise digital-to-analog converters for producing the stimulation pulses in accordance with digital signals defining at least the amplitude of the stimulation pulses;
    a first power source comprising an ultracapacitor that provides operating power for the circuit elements; and
    a volatile memory associated with the pulse generator for storing programming data; and
    a second power source that has higher voltage retention than the ultracapacitor, wherein the second power source is dedicated to the volatile memory and provides operating power for the volatile memory.

2. The stimulator of claim 1, wherein the ultracapacitor has a capacitive rating of greater than 0.1 farad, and the second power source has higher voltage retention than the ultracapacitor.

3. The stimulator of claim 1 further comprising charging circuitry that includes an inductor coil and a rectifier circuit, wherein said charging circuitry receives power from an external source through the coil, rectifies the received power with the rectifier circuit, and directs said rectified power to the ultracapacitor for the purpose of recharging the ultracapacitor.

4. The stimulator of claim 1, wherein the first power source is recharged with RF waves received from an external recharge transmitter unit.

5. The stimulator of claim 1, wherein the second power source is recharged with RF waves received from an external recharge transmitter unit.

6. The stimulator of claim 1, wherein the volatile memory comprises SRAM or DRAM.

7. The stimulator of claim 1, further comprising a recharge coil in electrical communication with the ultracapacitor, wherein the recharge coil is enclosed within a magnetically transparent material.

8. The stimulator of claim 7, further comprising one or more protection diodes in electrical communication with the recharge coil and the first power source, wherein the protection diodes prevent output voltage from exceeding a threshold value.

9. The stimulator of claim 8, wherein the threshold value is about 5V.

10. The stimulator of claim 1, further comprising a housing made of a magnetically transparent material.

11. The stimulator of claim 1, wherein the second power source comprises a battery.

12. The stimulator of claim 1, further comprising a nonvolatile memory, and wherein the ultracapacitor provides operating power for the nonvolatile memory.

13. A system for stimulating tissue comprising:
an implantable stimulator comprising:
pulse generator circuitry for producing stimulation pulses, wherein the pulse generator circuitry comprises at least one digital-to-analog converter for producing the stimulation pulses in accordance with digital signals defining at least the amplitude of the stimulation pulses;
a first power source comprising an ultracapacitor that provides operating power for said pulse generator circuitry;
a volatile memory for storing programming data and providing said programming data to the pulse generator circuitry; and
a second power source that has higher voltage retention than the first power source, wherein the second power source is dedicated to the volatile memory and provides operating power for the volatile memory; and
a remote programmer unit that transmits programming information to the implantable stimulator, wherein the programming information is stored in the volatile memory.

14. The system of claim 13, wherein a recharge transmitter transmits a first set of RF signals to the stimulator, wherein the first set of RF signals recharges the ultracapacitor.

15. The system of claim 14, wherein a recharge transmitter transmits a second set of RF signals to the stimulator, wherein the second set of RF signals recharges the second power source.

16. The system of claim 13, further comprising a recharge coil electrically coupled to the ultracapacitor, wherein the recharge coil is enclosed within a magnetically transparent material.

17. The system of claim 16, further comprising one or more protection diodes in electrical communication with the recharge coil and the first power source, wherein the protection diodes prevent output voltage from exceeding a threshold value.

18. The system of claim 17, wherein the threshold value is about 5V.

19. The system of claim 13, wherein the implantable stimulator is housed in a magnetically transparent material.

20. The system of claim 13, wherein the implantable stimulator further comprises a nonvolatile memory, and wherein the ultracapacitor provides operating power for the nonvolatile memory.

21. The system of claim 13, the volatile memory comprises SRAM or DRAM.

22. The system of claim 13, wherein the second power source comprises a battery.

23. The system of claim 13, wherein the ultracapacitor has a capacitive rating of greater than 0.1 farad, and the second power source has higher voltage retention than the ultracapacitor.

24. The system of claim 13, further comprising charging circuitry that includes an inductor coil and a rectifier circuit, wherein said charging circuitry receives power from an external source through the coil, rectifies the received power with the rectifier circuit, and directs said rectified power to the ultracapacitor for the purpose of recharging the ultracapacitor.

25. The system of claim 13, further comprising a remote recharge transmitter that transmits one or more sets of RF signals to the stimulator.

26. The system of claim 13, wherein the pulse generator circuitry produces stimulation pulses for stimulating a patient's tissue.

27. An implantable stimulator, comprising:
pulse generation circuitry for producing stimulation pulses, wherein the pulse generation circuitry comprises at least one digital-to-analog converter for producing the stimulation pulses in accordance with digital signals defining at least the amplitude of the stimulation pulses;
a volatile memory for storing data and for providing the data to the pulse generation circuitry;
a capacitor for providing operating power to the pulse generation circuitry; and
a battery for providing power only to the volatile memory.

28. The stimulator of claim 27, wherein the battery has higher voltage retention than the capacitor.

29. The stimulator of claim 27, wherein the capacitor has a capacitance of greater than 0.1 Farads.

30. The stimulator of claim 27, wherein the battery is recharged with RF waves received from an external recharge transmitter unit.

31. The stimulator of claim 27, wherein the capacitor is recharged with RF waves received from an external recharge transmitter unit.

32. The stimulator of claim 27, wherein the data is received as RF waves from an external programmer.

33. The stimulator of claim 27, wherein the pulse generation circuitry produces stimulation pulses for stimulating a patient's tissue.

* * * * *